United States Patent
Sixt

(10) Patent No.: US 10,316,149 B2
(45) Date of Patent: Jun. 11, 2019

(54) CROSSLINKABLE ORGANOPOLYSILOXANE COMPOSITIONS

(71) Applicant: Wacker Chemie AG, Munich (DE)

(72) Inventor: Torsten Sixt, Mehring (DE)

(73) Assignee: WACKER CHEMIE AG, Munich (DE)

(*) Notice: Subject to any disclaimer, the term of this patent is extended or adjusted under 35 U.S.C. 154(b) by 0 days.

(21) Appl. No.: 15/524,975

(22) PCT Filed: Nov. 5, 2015

(86) PCT No.: PCT/EP2015/075856
§ 371 (c)(1),
(2) Date: May 5, 2017

(87) PCT Pub. No.: WO2016/071469
PCT Pub. Date: May 12, 2016

(65) Prior Publication Data
US 2017/0342216 A1    Nov. 30, 2017

(30) Foreign Application Priority Data
Nov. 7, 2014 (DE) .......... 10 2014 222 826

(51) Int. Cl.
| C08G 77/26 | (2006.01) |
| C08L 83/08 | (2006.01) |
| C08G 77/04 | (2006.01) |
| C08G 77/06 | (2006.01) |
| C08G 77/18 | (2006.01) |
| C07F 7/18  | (2006.01) |

(52) U.S. Cl.
CPC ............. *C08G 77/26* (2013.01); *C08G 77/04* (2013.01); *C08G 77/06* (2013.01); *C08L 83/08* (2013.01); *C07F 7/1804* (2013.01); *C08G 77/18* (2013.01)

(58) Field of Classification Search
CPC ........ C08G 77/16; C08G 77/26; C07F 7/1836
See application file for complete search history.

(56) References Cited

U.S. PATENT DOCUMENTS

| 3,105,061 | A   |   | 9/1963  | Bruner |
| 5,110,967 | A   |   | 5/1992  | King et al. |
| 5,290,826 | A   |   | 3/1994  | Palmer |
| 5,300,612 | A   |   | 4/1994  | Saruyama |
| 5,391,680 | A   | * | 2/1995  | Maruyama ........... C09D 183/04 427/387 |
| 5,470,934 | A   |   | 11/1995 | Saruyama et al. |
| 6,254,811 | B1  |   | 7/2001  | Finger et al. |
| 2004/0122199 | A1 |   | 6/2004  | Scheim et al. |
| 2005/0085612 | A1 |   | 4/2005  | Schafer et al. |
| 2005/0131243 | A1 |   | 6/2005  | Herzig et al. |
| 2005/0272895 | A1 |   | 12/2005 | Ziche et al. |
| 2015/0218377 | A1 |   | 8/2015  | Schoeley |

FOREIGN PATENT DOCUMENTS

| AU | 198287935 A1   | 3/1983 |
| CA | 2056487 A1     | 6/1992 |
| DE | 1 295 834      | 5/1969 |
| DE | 198 55 619 A1  | 6/2000 |
| EP | 0074001 A1     | 3/1983 |
| EP | 0 575 863 B1   | 12/1993 |
| EP | 0 693 533 A1   | 1/1996 |
| EP | 0 776944 A1    | 6/1997 |
| EP | 1 006 146 A1   | 6/2000 |
| EP | 1 431 330 A1   | 6/2004 |
| EP | 1 541 615 A1   | 6/2005 |
| EP | 1539863 A1     | 6/2005 |
| EP | 1 735 369 B1   | 12/2006 |
| JP | 6383167 A      | 4/1988 |
| JP | 2015523427 T2  | 8/2015 |
| WO | 03/068845 A1   | 8/2003 |
| WO | 2004/026944 A1 | 4/2004 |
| WO | 2016/071469 A1 | 5/2016 |

* cited by examiner

*Primary Examiner* — Kuo Liang Peng
(74) *Attorney, Agent, or Firm* — Brooks Kushman P.C.

(57) ABSTRACT

Moisture curable RTV-1 compositions with rapid curing and a modulus which is adjustable over a wide range include organopolysiloxanes having on-chain and side-chain silicon-bonded α-aminoalkyl groups and at least on average two silicon-bonded alkoxy groups, trialkoxyorganylsilanes and/or tetraalkoxysilanes, and organopolysiloxanes bearing alkoxysilyl groups.

15 Claims, No Drawings

CROSSLINKABLE ORGANOPOLYSILOXANE COMPOSITIONS

CROSS REFERENCE TO RELATED APPLICATIONS

This application is the U.S. National Phase of PCT Appln. No. PCT/EP2015/075856 filed Nov. 5, 2015, which claims priority to German Application No. 10 2014 222 826.3 filed Nov. 7, 2014, the disclosures of which are incorporated in their entirety by reference herein.

BACKGROUND OF THE INVENTION

1. Field of the Invention

The invention relates to crosslinkable materials which are based on organosilicon compounds and which cure preferably to form materials of reduced modulus, to processes for producing them, and to their use.

2. Description of the Related Art

One-component silicone rubber mixtures which vulcanize to form elastomers at room temperature (RTV1) on ingress of water, and which are storable in the absence of water, are known. These products are used in large quantities, for example, as joint-sealing compounds in the construction industry. The basis for these RTV1 mixtures are polydiorganosiloxanes, terminated either with OH groups or with silyl groups which carry hydrolyzable groups. Through the chain length of the polymers it is possible to influence key properties of the RTV1 mixtures. The so-called modulus in particular, usually reported as secant modulus at an elongation of 100%, can be regulated by the chain length. For joint-sealing compounds in particular it is desirable for this modulus to be low, to minimize forces acting on the edges of the joint. For economic and technical reasons, however, there is only a limited range of polymer chain lengths available for the production of RTV1 mixtures. The high chain lengths that are necessary for very low-modulus sealants, in particular, result in very high viscosities on the part of the polymers, and so, because of the resultant stiff paste consistency, the ready-to-apply products require high forces for extrusion from the cartridge, and hence are hampered by disadvantages in processing.

Adjusting or lowering the modulus is a frequent topic of description in the patent literature. CA 2056487 A2 proposes incorporating mono-alkoxy-functional end groups into the polymer. These groups no longer exhibit virtually any reaction, and so lower the modulus. The latent alkoxy groups are a disadvantage in that they nevertheless display residual activity under elevated temperature and humidity influence, and may have adverse consequences for the vulcanizate properties.

EP-A 0776944 describes monofunctional siloxanes which exhibit adjustment of modulus non-functional terminal groups. While this does avoid the disadvantage of CA 2056487 A2, it nevertheless necessitates a separate, targeted preparation of such monofunctional siloxanes.

In order to avoid these difficulties, the principle of chain extension has been pursued for adjustment of modulus. U.S. Pat. No. 5,110,967 describes Si—N heterocyclic silanes, but specialty crosslinkers of this kind are not available on the market. Further difunctional silanes have been described in U.S. Pat. No. 5,290,826 (bisacetamidosilanes), DE 12 95 834 (bisacetoxysilanes), and EP 74 001 (bisaminosilanes), but these release basic or acidic elimination products and are therefore not suitable for surfaces which are not compatible with these elimination products. This is the case, for example, for marble or some metallic surfaces. Chain extension with acetamidosilane or aminosilane, moreover, still gives rise to an odor nuisance.

Difunctional dialkyl-dialkoxysilanes do not give off any corrosive byproducts, but are unsuitable, since they exhibit inadequate reactivity and display a significant effect only when added at a very high level, this being a disadvantage in terms of cost. In this regard, see U.S. Pat. No. 5,300,612, U.S. Pat. No. 5,470,934, and DE-A 198 55 619. EP-A 0575863B1 and EP-A 0 693 533 attempt to resolve this disadvantage by using short-chain siloxanes having two in-chain alkoxy functions. However, such siloxanes must be specifically produced and are still always too unreactive. Accordingly, they as well must be used in relatively large quantities. EP-A 1006146 describes mixed endblocking with a mixture of di- and trifunctional alkoxysilanes, with which a moderate modulus reduction effect can be obtained only by using comparatively large quantities of difunctional dimethoxydimethylsilane. This increases the weight loss and the emission of elimination products, and is detrimental to cost.

JP 63-83167 describes chain extension using difunctional α-amino-substituted alkoxysilanes, with distinct effects. The disadvantage of the proposed formulas, however, is the high quantity of difunctional α-silane, which has serious disadvantages in terms firstly of cost and secondly of shelf life. EP 1 735 369 B1 describes siloxanes having the feature of particularly quick-crosslinking preparations. These are based on pure α-aminosilane functionalization or else on mixed endblocking with secondary α-amino groups. The storage stability in the vulcanizate, however, is poor.

EP-A 1431330 describes an attempted solution with which good modulus adjustment results were achievable with low quantities of α-aminofunctional alkoxysilanes, but the storage stability could not be stabilized until isocyanate compounds were added. This is critical on account of the toxicity of isocyanates, and therefore has adverse consequences for the production and handling of such preparations.

The problems addressed by the invention are to provide crosslinkable compositions with a modulus which can be adjusted by targeted chain extension, which are largely isocyanate-free, and which at the same time are stable on storage and have good workability.

SUMMARY OF THE INVENTION

An object of the invention is thus crosslinkable organopolysiloxane compositions producible using
(A) organosilicon compounds comprising units of the formula $$[R^1{}_2NCR^4{}_2]_b SiR^3{}_c(OR^2)_a O_{(4-a-b-c)/2} \qquad (I),$$

where
$R^1$ may be identical or different and is a monovalent, optionally substituted hydrocarbyl radical,
$R^2$ may be identical or different and is a monovalent, optionally substituted hydrocarbyl radical,
$R^3$ may be identical or different and is a monovalent hydrocarbyl radical,
$R^4$ may be identical or different and is hydrogen atom or a monovalent, optionally substituted hydrocarbyl radical,
a is 0, 1, 2 or 3,
b is 0, 1 or 2, preferably 0 or 1, and
c is 0, 1, 2 or 3,
with the proviso that organosilicon compound (A) has at least one unit of the formula (I) where a=b=c=1, the sum is a+b+c=2 in at least 50% of the units of the formula (I), and the organosilicon compound contains at least 2 groups —OR$^2$,
optionally (B) silanes of the formula $$R^1{}_2NCR^4{}_2SiR^3(OR^2)_2 \qquad (XI),$$

where $R^1$, $R^2$, $R^3$, and $R^4$ may be identical or different and have one of the definitions indicated above,
(C) silanes of the formula $$R^6{}_dSi(OR^7)_{4-d} \qquad (II)$$

and/or their partial hydrolysates having up to 10 silicon atoms, where
$R^6$ has a definition indicated for $R^3$,
$R^7$ may be identical or different and is a monovalent, optionally substituted hydrocarbyl radical or a radical —N=CR$^5{}_2$, $R^5$ may be identical or different and has a definition indicated for $R^2$, and
d is 0 or 1,
and
(D) organosilicon compounds selected from
(D1) compounds comprising units of the formulae $$R^8{}_mSi(OR^9)_{3-m}O_{1/2} \qquad (III),$$

$$R^8{}_mSi(OR^9)_{2-m}O_{2/2} \qquad (IV), \text{ and}$$

$$R^8{}_mSi(OR^9)_{1-m}O_{3/2} \qquad (V),$$

where
$R^8$ may be identical or different and in each case, independently of any other, is a monovalent hydrocarbyl radical,
$R^9$ may be identical or different and in each case, independently of any other, is a monovalent hydrocarbyl radical, and
m in each case, independently of any other, has the definition of 0 or 1,
with the proviso that compound (D1) has at least 3 groups —OR$^9$ per molecule and has a weight-average molecular weight Mw of 1000 to 3000 g/mol,
(D2) compounds of the formula $$(R^{10}O)_3Si—R^{11}—Si(OR^{10})_3 \qquad (VII),$$

where
$R^{10}$ may be identical or different and is a monovalent, optionally substituted hydrocarbyl radical which may be interrupted by heteroatoms,
$R^{11}$ may be identical or different and is a divalent, optionally substituted hydrocarbyl radical which may be interrupted by heteroatoms,
and
(D3) compounds comprising units of the formulae $$R^8{}_3SiO_{1/2} \qquad (XII),$$

$$SiO_{4/2} \qquad (VI), \text{ and}$$

$$R^8{}_mSi(OR^9)_{1-m}O_{3/2} \qquad (V)$$

and also, optionally, units of the formulae (III) and (IV), where
$R^8$, $R^9$ and m have a definition indicated for them above, with the proviso that m is 0 and compound (D3) has at least 3 groups —OR$^9$ per molecule and has a weight-average molar weight Mw of 1000 to 4000 g/mol, and mixtures containing at least one of D1, D2, and/or D3.

For the purposes of the present invention, the term "organopolysiloxanes" is intended to encompass polymeric, oligomeric, and dimeric siloxanes, in which some of the silicon atoms may also be joined to one another by groups other than oxygen, such as via —N— or —C—, for instance.

The organosilicon compounds (A) used in accordance with the invention may be any desired, conventional organopolysiloxanes having at least one Si-bonded [R$^1{}_2$NCR$^4{}_2$] radical, where $R^1$ and $R^4$ are as defined above.

The organosilicon compounds (A) used in accordance with the invention are preferably compounds consisting of units of the formula (I).

The organosilicon compounds (A) used in accordance with the invention are preferably compounds comprising units (Ia) —R$_2$SiO— and (Ib) [R$^1{}_2$NCR$^4{}_2$]SiR$^3$ (OR$^2$) O$_{1/2}$ and also, optionally, (Ic) [R$^1{}_2$NCR$^4{}_2$]SiR$^3$O$_{(2/2)}$, where the radicals and indices have the definition stated above.

In preferably at least 80%, more preferably in 95 to 99.9%, of all units of the formula (I) in organopolysiloxane (A) of component (A), the units are of the formula (I) with a=b=0 and c=2.

The organopolysiloxanes (A) used in accordance with the invention preferably have a total Si-bonded R$^2$O group content of 400 to 12 000 ppm by weight, more preferably of 500 to 6000 ppm by weight, and most preferably 1000 to 4000 ppm by weight, where $R^2$ is as defined above.

The organopolysiloxanes (A) used in accordance with the invention preferably have a number-average molecular weight Mn preferably in the range from 15,000 to 150,000 g/mol, more preferably from 30,000 to 125,000 g/mol, and most preferably from 40,000 to 100,000 g/mol.

The organopolysiloxanes (A) used in accordance with the invention are preferably liquid at room temperature under the pressure of the surrounding atmosphere, i.e., at between 900 and 1100 hPa.

The organopolysiloxanes (A) used in accordance with the invention are commercial products and/or are preparable by methods common in chemistry.

The organopolysiloxanes (A) used in accordance with the invention may, for example, be implemented by reaction of OH-siloxanes with chain extenders, optionally in combination with crosslinkers.

With particular preference, the organosilicon compounds (A) used in accordance with the invention are compounds preparable by reaction of organosilicon compounds having at least two OH groups (A0) with silanes (B) and silanes (C') of the formula R$^3$Si(OR$^2$)$_3$ or Si(OR$^2$)$_4$, optionally in the presence of catalyst (K) and, optionally, of further substances, and $R^2$ and $R^3$ have one of the definitions indicated for them above.

The organosilicon compounds having at least two OH groups (A0) are preferably substantially linear organopolysiloxanes which are terminated at both ends by Si-bonded hydroxyl groups.

Organosilicon compounds (A0) preferably have an OH content of 230 to 25,000 ppm by weight, more preferably of 250 to 1250 ppm by weight, and most preferably of 300 to 1000 ppm by weight.

Organosilicon compounds (A0) are very preferably compounds of the formula $$HO(R_2SiO)_nH \qquad (VIII),$$

where
R may be identical or different and is a monovalent, optionally substituted hydrocarbyl radical and
n is an integer from 200 to 2000, preferably from 400 to 1700, and more preferably from 500 to 1500, and more particularly are α,ω-dihydroxydialkylpolysiloxanes, very preferably α,ω-dihydroxypolydimethylsiloxanes.

Examples of radicals R are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radical, hexyl radicals such as the n-hexyl radical, heptyl radicals, such as the n-heptyl radical, octyl radicals, such as the n-octyl radical and isooctyl radicals such as the 2,2,4-trimethylpentyl radical, nonyl radicals such as the n-nonyl radical, decyl radicals such as the n-decyl radical, and dodecyl radicals such as the n-dodecyl radical; cycloalkyl radicals such as cyclopentyl, cyclohexyl, cycloheptyl, and methylcyclohexyl radicals; alkenyl radicals such as the vinyl, 5-hexenyl, cyclohexenyl, 1-propenyl, allyl, 3-butenyl, and 4-pentenyl radicals; alkynyl radicals such as the ethynyl, propargyl, and 1-propynyl radical; aryl radicals such as the phenyl radical; alkaryl radicals such as the o-, m-, and p-tolyl radicals; and aralkyl radicals such as the benzyl radical, and the α- and the β-phenylethyl radicals.

Examples of substituted radicals R are haloalkyl radicals such as the chloromethyl radical, the 3,3,3-trifluoro-n-propyl radical, and the 2,2,2,2',2',2'-hexafluoroisopropyl radical, the heptafluoroisopropyl radical, and haloaryl radicals such as the o-, m-, and the p-chlorophenyl radicals, and all aforementioned radicals substituted by epoxy-functional groups, carboxyl groups, enamine groups, amino groups, aminoethylamino groups, aryloxy groups, acryloyloxy groups, methacryloyloxy groups, hydroxyl groups, and halogen groups.

Radical R preferably comprises monovalent hydrocarbyl radicals having 1 to 18 carbon atoms, optionally substituted by halogen atoms, amino groups, ether groups, ester groups, epoxy groups, mercapto groups or (poly)glycol radicals, the latter being constructed from oxyethylene units and/or oxypropylene units, and which more preferably comprises alkyl radicals having 1 to 12 carbon atoms, more particularly the methyl radical.

Examples of organosilicon compounds (A0) are
$(HO)Me_2SiO[SiMe_2O]_xSiMe_2(OH)$,
$(HO)Me_2SiO[SiMe_2O]_x[SiMePhO]_ySiMe_2(OH)$, and
$(HO) Me_2SiO [SiMe_2O]_x[SiPh_2O]_ySiMe_2 (OH)$
where Me is methyl radical and Ph is phenyl radical, it being possible for the individual units to be distributed statistically in the molecule, where x is a number from 200 to 2000, preferably 300 to 1100, more preferably 500 to 1500, and y is a number such that y/x is preferably 0.01 to 0.1.

The organosilicon compounds (A0) used in accordance with the invention preferably have a viscosity of 1000 to 700,000 mPas, more preferably of 6000 to 400,000 mPas, and most preferably of 10,000 to 250,000 mPas, in each case at 25° C.

The organosilicon compounds (A0) are commercial products and/or can be prepared by methods common in silicon chemistry.

Examples of radicals $R^1$, $R^2$, $R^3$, and $R^4$ are the examples indicated for radical R.

Radical $R^1$ preferably comprises alkyl radicals having 1 to 6 carbon atoms, more preferably the ethyl, n-propyl, n-butyl, isopropyl or isobutyl radical, more particularly the ethyl, n-propyl or n-butyl radical.

Radical $R^2$ preferably comprises alkyl radicals having 1 to 6 carbon atoms, more preferably the methyl and ethyl radical.

Radical $R^3$ preferably comprises monovalent hydrocarbyl radicals having 1 to 18 carbon atoms, more preferably alkyl radicals having 1 to 12 carbon atoms, and most preferably the methyl radical.

Radical $R^4$ preferably comprises hydrogen and hydrocarbyl radicals having 1 to 20 carbon atoms, more preferably hydrogen.

Examples of the silanes (B) used in accordance with the invention are $(H_3C)_2N-CH_2-Si(CH_3)(OCH_3)_2$, $(H_3C)_2N-CH_2-Si(CH_3)(OCH_2CH_3)_2$, $(H_3C-CH_2)_2N-CH_2-Si(CH_3)(OCH_3)_2$, $(H_3C-CH_2)_2N-CH_2-Si(CH_3)(OCH_2CH_3)_2$, $(CH_3-(CH_2)_2)_2N-CH_2-Si(CH_3)(OCH_3)_2$, $(CH_3-(CH_2)_2)_2N-CH_2-Si(CH_3)(OCH_2CH_3)_2$, $((CH_3)_2CH)_2N-CH_2-Si(CH_3)(OCH_3)_2$, $((CH_3)_2CH)_2N-CH_2-Si(CH_3)(OCH_2CH_3)_2$, $(CH_3-(CH_2)_3)_2N-CH_2-Si(CH_3)(OCH_3)_2$, $(CH_3-(CH_2)_3)_2N-CH_2-Si(CH_3)(OCH_2CH_3)_2$, $(CH_3CH_2 (CH_3) CH)_2N-CH_2-Si(CH_3)(OCH_3)_2$, $(CH_3CH_2 (CH_3) CH)_2N-CH_2-Si(CH_3)(OCH_2CH_3)_2$, $C_6H_5 (CH_3)N-CH_2-Si(CH_3)(OCH_2CH_3)_2$, $C_6H_5 (CH_3)N-CH_2-Si(CH_3)(OCH_3)_2$, $C_6H_{11} (CH_3)N-CH_2-Si(CH_3)(OCH_2CH_3)_2$, and $C_6H_{11} (CH_3)N-CH_2-Si(CH_3)(OCH_3)_2$.

The silanes (B) used in accordance with the invention are preferably $(CH_3-(CH_2)_3)_2N-CH_2-Si(CH_3)(OCH_3)_2$, $(CH_3-(CH_2)_3)_2N-CH_2-Si(CH_3)(OCH_2CH_3)_2$, $(H_3C-CH_2)_2N-CH_2-Si(CH_3)(OCH_2CH_3)_2$, $(H_3C-CH_2)_2N-CH_2-Si(CH_3)(OCH_3)_2$, $(CH_3-(CH_2)_2)_2N-CH_2-Si(CH_3)(OCH_3)_2$, $(CH_3-(CH_2)_2)_2N-CH_2-Si(CH_3)(OCH_2CH_3)_2$, $((CH_3)_2CH)_2N-CH_2-Si(CH_3)(OCH_3)_2$, and $((CH_3)_2CH)_2N-CH_2-Si(CH_3)(OCH_2CH_3)_2$, more preferably $(H_3C-CH_2)_2N-CH_2-Si(CH_3)(OCH_2CH_3)_2$, $(H_3C-CH_2)_2N-CH_2-Si(CH_3)(OCH_3)_2$, $(CH_3-(CH_2)_3)_2N-CH_2-Si(CH_3)(OCH_3)_2$, and $(CH_3-(CH_2)_3)_2N-CH_2-Si(CH_3)(OCH_2CH_3)_2$.

Component (A) used in accordance with the invention is preferably prepared using chain extenders (B) in amounts such that the molar ratio of component (B) to Si—OH in component (A0) is less than 1, preferably less than 0.6, and more preferably less than 0.4. The molar ratio of component (B) to Si—OH in component (A0) is preferably greater than 0.005, more preferably greater than 0.01.

The silanes (B) used in accordance with the invention are commercial compounds and/or are preparable by processes common in chemistry.

Examples of the silanes (C') used in accordance with the invention are tetraalkoxysilanes and organyltrialkoxysilanes, such as methyltrimethoxysilane, ethyltrimethoxysilane, n-propyltrimethoxysilane, vinyltrimethoxysilane, methyltriethoxysilane, ethyltriethoxysilane, n-propyltriethoxysilane, and vinyltriethoxysilane, and also organyltrioximosilanes, such as methyltris(methylethylketoximo)silane and vinyltris(methylethylketoximo)silane, and also the partial hydrolysates of the aforementioned silanes, having not more than 10 silicon atoms.

The silanes (C') used in accordance with the invention are preferably organyltrialkoxysilanes and/or their partial hydrolysates having not more than 10 silicon atoms, more preferably methyltrimethoxysilane and vinyltrimethoxysilane, and also the partial hydrolysates of the aforementioned silanes having not more than 10 silicon atoms.

Component (A) used in accordance with the invention is preferably prepared using silanes (C') preferably in amounts of 1 to 5 parts by weight, more preferably 1.5 to 2.5 parts by weight, based in each case on 100 parts by weight of component (A0).

The preparation of component (A) in accordance with the invention is carried out preferably in the presence of catalyst (K). Examples of the optionally employed catalysts (K) are all catalysts which are useful in reactions of Si-bonded organyloxy groups with Si—OH groups.

The catalysts (K) employed optionally in accordance with the invention are preferably metal chelates and phosphoric esters, more preferably titanium chelates, zinc acetylacetonate, aluminum acetylacetonate, 2-ethylhexyl phosphate, di(2-ethylhexyl) phosphate, and diethylamine, di-n-propylamine, di-n-butylamine, di-n-hexylamine, diisopropylamine, diisobutylamine, diisohexylamine or aminoalkylsilanes such as aminopropyltrimethoxysilane, aminopropyltriethoxysilane, aminoethyl-aminopropyltrimethoxysilane or aminoethyl-aminopropyltriethoxysilane and/or combinations thereof, more preferably zinc acetylacetonate, aluminum acetylacetonate, di-n-propylamine, di-n-butylamine, di-n-hexylamine, diisopropylamine, diisobutylamine, diisohexylamine or combinations thereof.

If catalysts (K) are used for preparing siloxanes (A), as is preferred, the amounts are preferably 0.001 to 1 part by weight, more preferably 0.005 to 0.1 part by weight, based in each case on 100 parts by weight of component (A0).

Component (A) used in accordance with the invention is preferably prepared in the absence of moisture at temperatures of 10 to 100° C., preferably 20 to 80° C., under pressures between 0.1 to 10 atmospheres, preferably between 0.8 to 8 atmospheres.

If component (A) used in accordance with the invention is prepared in the presence of a gas phase, in other words in the form of an open or partially filled reaction space, then preparation takes place preferably with exclusion of moisture, with dried air or dried nitrogen being passed over or used for blanketing, at temperatures between 10° C. and 60° C., more preferably between 20° C. and 50° C., and at pressures of between 0.1 and 1 atmosphere, more preferably between 0.6 to 1 atmosphere.

If component (A) used in accordance with the invention is prepared in a closed system in the absence of a gas phase, in other words in the form of a largely filled reaction space with a fill level of more than 90%, preparation preferably takes place at temperatures between 10° C. and 80° C., more preferably between 20° C. and 60° C., and at pressures of between 0.1 and 8 atmospheres, more preferably between 0.8 and 6 atmospheres.

The organosilicon compounds (A) used in accordance with the invention are, more particularly, compounds preparable by reaction of organosilicon compounds having at least two OH groups (A0) with silanes (B) and silanes (C') of the formula $R^3Si(OR^2)_3$ in the presence of catalyst (K), (B) being used in amounts such that the molar ratio of component (B) to Si—OH in component (A0) is less than 1, preferably less than 0.6 and more preferably less than 0.4, with $R^2$ having the definition indicated for it above.

Preferably in this case the silanes are used in a molar ratio of silanes (C') to chain extenders (B) of greater than 20:1, more preferably greater than 30:1, and most preferably greater than 40:1. The molar ratio of silanes (C') to chain extenders (B) is preferably less than 800:1, more preferably less than 300:1, and most preferably less than 150:1.

Examples of organopolysiloxanes (A) used in accordance with the invention are
$(Et_2NCH_2)(Me)(OMe)SiO$—$[SiMe_2O]_zSiMe_2$—O—Si(Me)(OMe)$_2$,
$(Et_2NCH_2)(Me)(OMe)SiO$—$[SiMe_2O]_zSiMe_2$—O—Si(Vi)(OMe)$_2$,
$(Bu_2NCH_2)(Me)(OMe)SiO$—$[SiMe_2O]_zSiMe_2$—O—Si(Me)(OMe)$_2$,
$(Bu_2NCH_2)(Me)(OMe)SiO$—$[SiMe_2O]_zSiMe_2$—O—Si(Vi)(OMe)$_2$,
$(Et_2NCH_2)(Me)(OMe)SiO$—$[SiMe_2O]_zSiMe_2$—O—Si(Me)(OEt)$_2$,
$(Et_2NCH_2)(Me)(OMe)SiO$—$[SiMe_2O]_zSiMe_2$—O—Si(Vi)(OEt)$_2$,
$(Bu_2NCH_2)(Me)(OMe)SiO$—$[SiMe_2O]_zSiMe_2$—O—Si(Me)(OEt)$_2$,
$(Bu_2NCH_2)(Me)(OMe)SiO$—$[SiMe_2O]_zSiMe_2$—O—Si(Vi)(OEt)$_2$,
$(Et_2NCH_2)(Me)(OEt)SiO$—$[SiMe_2O]_zSiMe_2$—O—Si(Me)(OMe)$_2$,
$(Et_2NCH_2)(Me)(OEt)SiO$—$[SiMe_2O]_zSiMe_2$—O—Si(Vi)(OMe)$_2$,
$(Bu_2NCH_2)(Me)(OEt)SiO$—$[SiMe_2O]_zSiMe_2$—O—Si(Me)(OMe)$_2$,
$(Bu_2NCH_2)(Me)(OEt)SiO$—$[SiMe_2O]_zSiMe_2$—O—Si(Vi)(OMe)$_2$,
$(Et_2NCH_2)(Me)(OEt)SiO$—$[SiMe_2O]_zSiMe_2$—O—Si(Me)(OEt)$_2$,
$(Et_2NCH_2)(Me)(OEt)SiO$—$[SiMe_2O]_zSiMe_2$—O—Si(Vi)(OEt)$_2$,
$(Bu_2NCH_2)(Me)(OEt)SiO$—$[SiMe_2O]_zSiMe_2$—O—Si(Me)(OEt)$_2$, and
$(Bu_2NCH_2)(Me)(OEt)SiO$—$[SiMe_2O]_zSiMe_2$—O—Si(Vi)(OEt)$_2$,
$(Vi)(MeO)_2SiO$—$[SiMe_2O]_z(Bu_2NCH_2)(Me)$ SiO—$[SiMe_2O]_zSiMe_2$—O—Si(Vi) (OMe)$_2$,
$(Vi)(MeO)_2SiO$—$[SiMe_2O]_z(Et_2NCH_2)(Me)$ SiO—$[SiMe_2O]_zSiMe_2$—O—Si(Vi) (OMe)$_2$,
$(Me)(MeO)_2SiO$—$[SiMe_2O]_z(Bu_2NCH_2)(Me)$ SiO—$[SiMe_2O]_zSiMe_2$—O—Si(Vi) (OMe)$_2$, and
$(Me)(MeO)_2SiO$—$[SiMe_2O]_z(Bu_2NCH_2)(Me)$ SiO—$[SiMe_2O]_zSiMe_2$—O—Si(Me) (OMe)$_2$,
where
$(Et_2NCH_2)(Me)(OMe)SiO$—$[SiMe_2O]_zSiMe_2$—O—Si(Me)(OMe)$_2$,
$(Et_2NCH_2)(Me)(OMe)SiO$—$[SiMe_2O]_zSiMe_2$—O—Si(Vi)(OMe)$_2$,
$(Bu_2NCH_2)(Me)(OMe)SiO$—$[SiMe_2O]_zSiMe_2$—O—Si(Me)(OMe)$_2$, and
$(Bu_2NCH_2)(Me)(OMe)SiO$—$[SiMe_2O]_zSiMe_2$—O—Si(Vi)(OMe)$_2$,
$(Vi)(MeO)_2SiO$—$[SiMe_2O]_zBu_2NCH_2)(Me)$ SiO—$[SiMe_2O]_zSiMe_2$—O—Si(Vi) (OMe)$_2$, and
$(Vi)(MeO)_2SiO$—$[SiMe_2O]_z(Et_2NCH_2)(Me)$ SiO—$[SiMe_2O]_zSiMe_2$—O—Si(Vi) (OMe)$_2$
are preferred, with Me being the methyl radical, Et being the ethyl radical, Bu being the butyl radical, and Vi being the vinyl radical, with a number of repeating units z of 200 to 2000, preferably 300 to 1500, and more preferably 500 to 1100.

The crosslinkable compositions of the invention are preferably prepared without using silanes (B).

If silanes (B) are used for preparing the materials of the invention, the amounts involved are preferably not more than 1.0 part by weight, more preferably 0.1 to 0.5 part by weight, based in each case on 100 parts by weight of component (A).

Examples of radical $R^6$ are the examples of hydrocarbyl radicals indicated above for radical R.

Radical $R^6$ preferably comprises monovalent hydrocarbyl radicals having 1 to 18 carbon atoms, more preferably alkyl radicals having 1 to 12 carbon atoms, and most preferably the methyl and vinyl radical.

Examples of radical $R^5$ are the examples indicated above for radical R. Radical $R^5$ preferably comprises monovalent hydrocarbyl radicals having 1 to 18 carbon atoms, more preferably the methyl, ethyl, propyl, isopropyl or isobutyl radicals.

Examples of radical $R^7$ are the examples indicated above for radical R, and also —N=C(CH$_3$)(C$_2$H$_5$), —N=C(CH$_3$)$_2$, —N=C(CH$_3$)(C$_3$H$_7$), and —N=C(CH$_3$)(C$_4$H$_9$).

Radical $R^7$ preferably comprises alkyl radicals and also radicals —N=$CR^5_2$, more preferably alkyl radicals having 1 to 6 carbon atoms, more particularly the methyl and ethyl radicals.

In formula (II), d preferably has the definition of 1.

Examples of silanes (C) used in accordance with the invention are the examples indicated above for component (C'). The silanes (C) used in accordance with the invention are preferably organyltrialkoxysilanes and/or their partial hydrolysates having not more than 10 silicon atoms, more preferably methyltrimethoxysilane and vinyltrimethoxysilane, and also the partial hydrolysates of the aforementioned silanes having not more than 10 silicon atoms. If partial hydrolysates of silanes of the formula (II) are used as component (C), preference is given to those having not more than 6 silicon atoms.

If silanes (C') are used for preparing component (A), component (C) more preferably comprises the same silanes, For preparing the compositions of the invention, silanes (C) and/or their partial hydrolysates having not more than 10 silicon atoms are preferably used in amounts of 1 to 20 parts by weight, more preferably 1.5 to 7 parts by weight, in each case based on 100 parts by weight of component (A).

Examples of radicals $R^8$ and $R^9$ are the examples indicated above for radical R.

Radical $R^8$ preferably comprises a methyl, ethyl, propyl or phenyl radical, more preferably a methyl or phenyl radical, most preferably the methyl radical.

Radical $R^9$ preferably comprises a methyl, ethyl or propyl radical, more preferably a methyl or ethyl radical, most preferably the ethyl radical.

Preferably m has the definition of 1.

The compounds (D1) used in accordance with the invention contain units of the formulae (III), (IV), and (V) in amounts preferably totaling at least 80 mol %, more preferably at least 95 mol %, and most preferably at least 98.5 mol %.

The compounds (D1) used in accordance with the invention contain at least 20 mol % of units of the formula (V), preferably 20 to 60 mol % and more preferably 25 to 50 mol %.

The compounds (D1) used in accordance with the invention preferably contain 5 to 30 mol % of units of the formula (III).

The compounds (D1) used in accordance with the invention preferably contain 20 to 50 mol % of units of the formula (IV).

The compounds (D1) used in accordance with the invention preferably contain 20 to 60 mol % of units of the formula (V), 5 to 30 mol % of units of the formula (III), and 20 to 50 mol % of units of the formula (IV).

The compounds (D1) used in accordance with the invention may also comprise yet further units in addition to the units of the formulae (III), (IV), and (V), such as, for example, $SiO_{4/2}$ (VI), $R^8_2Si(OR^9)O_{1/2}$ (IX) or $R^8_2SiO_{2/2}$ (X), in each case $R^8$ and $R^9$ having one of the above-stated definitions.

The compounds (D1) used in accordance with the invention preferably consist of units of the formulae (III), (IV), (V), and optionally (VI), optionally (IX), and also, optionally, (X).

Compound (D1) preferably comprises per molecule at least 5 groups —$OR^9$ where $R^9$ is defined as stated above.

The compounds (D1) used in accordance with the invention are preferably resinous products, more preferably silicone resins which are liquid at room temperature under a pressure of 1013 hPa, thereby substantially facilitating their technical usefulness.

The compounds (D1) used in accordance with the invention preferably have a viscosity of 1 to 100 mPa·s, more preferably 10 to 40 mPa·s, and most preferably from 15 to 30 mPa·s, in each case at 25° C.

The compounds (D1) used in accordance with the invention preferably have a density of 0.9 to 1.3 g/cm³, more preferably 0.95 to 1.20 g/cm³, and most preferably from 1.05 to 1.18 g/cm³, in each case at 25° C.

Although not expressed by the formulae (III), (IV), (V), and (IX), the compounds (D1) used in accordance with the invention may as a result of their preparation, include up to 1 wt %, preferably less than 0.8 wt %, and more preferably less than 0.5 wt %, of residual Si—OH as an impurity.

The compounds (D1) used in accordance with the invention preferably have a weight-average Mw of preferably 2000 to 3000 g/mol.

The organosilicon compounds (D1) are commercial products and/or can be prepared by methods commonplace within silicon chemistry. For example, the compounds (D1) used in accordance with the invention may be prepared by hydrolysis and subsequent condensation of alkyltrialkoxysilanes. They are preferably prepared from methyl-, ethyl- and vinyltrialkoxysilanes, more preferably methoxy- and ethoxysilanes.

If component (D1) is used in preparing the materials of the invention, the amounts are preferably 0.01 to 50 parts by weight, more preferably 0.1 to 20 parts by weight, and most preferably 1 to 10 parts by weight, based in each case on 100 parts by weight of component (A).

Compounds (D1) can be used directly or in a mixture with low-boiling organic solvents, such as alcohols or toluene, for preparing the materials of the invention. If compounds (D1) are used in a mixture with organic solvents, which is not preferred, the amounts involved are preferably not more than 5 wt %, based on the total weight of the mixture.

Examples of radical $R^{10}$ are the examples indicated above for radical R. Radical $R^{10}$ preferably comprises alkyl radicals having 1 to 4 carbon atoms, more preferably methyl or ethyl radical.

Examples of divalent radicals $R^{11}$ are alkylene radicals such as the ethylene, n-propylene, isopropylene, n-butylene, isobutylene, n-pentylene, and isopentylene radicals, hexylene radicals such as the n-hexylene radical, heptylene radicals such as the n-heptylene radical, octylene radicals such as the n-octylene radical and isooctylene radicals, nonylene radicals such as the n-nonylene radical, decylene radicals such as the n-decylene radical, dodecylene radicals, such as the n-dodecylene radical; alkenylene radicals such as the vinylene radical, propylidene or butylidene radicals; cycloalkylene radicals such as the cyclopentylene, cyclohexylene, cycloheptylene, and methylcyclohexylene radicals; and also arylene radicals such as the phenylene radical.

Radicals $R^{11}$ are preferably ethylene, n-butylene or vinylene radicals.

Examples of organosilicon compounds (D2) are 1,2-bis(triethoxysilyl)ethane, 1,1-bis(triethoxysilyl)ethane, 1,2-bis(trimethoxysilyl)ethane, 1,1-bis(trimethoxysilyl)ethane, 1,4-bis(triethoxysilyl)butane, 1,4-bis(trimethoxysilyl)butane, 1,2-bis(triethoxysilyl)ethene, 1,1-bis(triethoxysilyl)ethene, 1,2-bis(trimethoxysilyl)ethene, and 1,1-bis(trimethoxysilyl)ethene.

Organosilicon compounds (D2) are preferably 1,2-bis(triethoxysilyl)ethane, 1,1-bis(triethoxysilyl)ethane, 1,2-bis (trimethoxysilyl)ethane or 1, 1-bis(trimethoxysilyl)-ethane, or 1,2-bis(triethoxysilyl)ethene or 1,2-bis(trimethoxysilyl) ethene.

If component (D2) is used in preparing the materials of the invention, the amounts involved are preferably 0.05 to 3 parts by weight, more preferably 0.1 to 2 parts by weight, and most preferably 0.1 to 1 part by weight, based in each case on 100 parts by weight of component (A).

The compounds (D3) used in accordance with the invention contain units of the formulae (XII), (VI), and (V) and also, optionally, (III) and optionally (IV), in amounts preferably totaling at least 80 mol %, more preferably at least 95 mol %, and most preferably at least 98.5 mol %.

The compounds (D3) used in accordance with the invention preferably contain 35 to 70 mol % of units of the formula (XII), more preferably 45 to 65 mol %, and most preferably 50 to 63 mol %.

The compounds (D3) used in accordance with the invention preferably contain 25 to 60 mol % of units of the formula (VI), more preferably 30 to 50 mol %, and most preferably 35 to 48 mol %.

The compounds (D3) used in accordance with the invention preferably contain preferably 0.5 to 10 mol % of units of the formula (V) where m is 0, more preferably in amounts of 2 to 8 mol %, most preferably in amounts of 2 to 6 mol %.

The compounds (D3) used in accordance with the invention preferably contain 35 to 70 mol % of units of the formula (XII), 25 to 60 mol % of units of the formula (VI), and 0.5 to 10 mol % of units of the formula (V) where m is 0. More preferably, the compounds (D3) contain 45 to 65 mol % of units of the formula (XII), 2 to 8 mol % of units of the formula (V) with the definition m=0, and 30-50 mol % of units of the formula (VI).

The compounds (D3) used in accordance with the invention may also comprise yet further units as well as the units of the formulae (XII), (V) with m=0, and (VI), and also, optionally, (III) and optionally (IV), such as, for example, $R^8_2Si(OR^9)O_{1/2}$ (IX) or $R^8_2SiO_{2/2}$ (X), in each case with $R^8$ and $R^9$ having one of the above-stated definitions.

The compounds (D3) used in accordance with the invention preferably consist of units of the formulae (XII), (VI), and (V) and also, optionally, (III), optionally (IV), optionally (IX), and optionally (X).

The compounds (D3) used in accordance with the invention are preferably resinous products, more preferably silicone resins which at room temperature under a pressure of 1013 hPa are liquid or soluble in silicone oil or silanes (C), thereby substantially facilitating the technical usefulness.

The compounds (D3) used in accordance with the invention preferably have a viscosity of 0.1 to 200 Pa·s, more preferably 0.10 to 100 Pa·s.

The compounds (D3) used in accordance with the invention preferably have a density of 0.9 to 1.3 g/cm³, more preferably 0.95 to 1.20 g/cm³, and most preferably from 1.0 to 1.15 g/cm³, in each case at 25° C.

Although not expressed by the formulae (III), (IV), (V), and (IX), the compounds (D3) used in accordance with the invention may as a result of their preparation, contain up to 1 wt %, preferably less than 0.8 wt %, more preferably less than 0.5 wt %, and most preferably not more than 2500 ppm by weight of residual Si—OH.

The compounds (D3) used in accordance with the invention have a weight-average Mw of preferably 1000 to 3000 g/mol, more preferably 1250 to 2000 g/mol.

The organosilicon compounds (D3) are commercial products and/or can be prepared by methods which are commonplace within silicon chemistry. For example, the compounds (D3) used in accordance with the invention may be prepared by hydrolysis of alkyltetraalkoxysilanes and subsequent cocondensation with trimethylsilanol. They are preferably prepared from tetraethyl silicates and trimethylsilanol.

If component (D3) is used in preparing the materials of the invention, the amounts are preferably 0.01 to 50 parts by weight, more preferably 0.1 to 20 parts by weight, and most preferably 1 to 10 parts by weight, based in each case on 100 parts by weight of component (A).

The materials of the invention can be prepared using compounds (D3) directly or in a mixture with low-boiling organic solvents, such as alcohols or toluene. If compounds (D3) are used in a mixture with organic solvents, which is not preferred, the amounts are preferably not more than 10 wt %, based on the total weight of the mixture.

As component (D), then, it is possible to use exclusively compounds (D1) or exclusively compounds (D2) or exclusively compounds (D3), or mixtures of at least two of the compounds (D1), (D2), and (D3), it being preferred as component (D) to use exclusively compounds (D1), (D2) or (D3) or mixtures of compounds (D1) and (D2) or mixtures of (D2) and (D3), more preferably exclusively (D1) or exclusively (D2) or mixtures of (D1) and (D2).

In addition to the components (A), optionally (B), and components (C), and (D), the materials of the invention may, then, comprise all further substances which are useful in materials crosslinkable by condensation reaction, such as, for example, catalysts (E), fillers (F), plasticizers (G), adhesion promoters (H), stabilizers (J), and additives (L), where components (F), (G), (H), (J), and (L) are different from components (A), (B), (C), and (D).

The crosslinkable materials of the invention are preferably prepared using catalysts (E). These may be any desired condensation catalysts which are useful in materials which are storable in the absence of water and which crosslink to elastomers on ingress of water at room temperature.

Examples of such condensation catalysts (E) are organic compounds of calcium, strontium, barium, copper, silver, tin, zinc, zirconium, titanium, bismuth, lead, iron, and aluminum. Preferred among these condensation catalysts are alkyl titanates, alkyl zirconates, zinc carboxylates, titanium chelates, and organotin compounds, such as di-n-butyltin diacetate, di-n-butyltin dilaurate, di-n-octyltin diacetate, di-n-octyltin dilaurate, and reaction products of silane or oligomer thereof, containing per molecule, as hydrolyzable groups, at least two monovalent hydrocarbyl radicals which are bonded via oxygen to silicon and which are optionally substituted by an alkoxy group, with diorganotin diacylate or diorganotin oxide, with all of the valences of the tin atoms in these reaction products being satisfied by oxygen atoms of the moiety ≡SiOSn≡ and/or by SnC-bonded, monovalent organic radicals. Further examples of condensation catalysts (E) are basic organic compounds such as, for example, diazabicycloundecene, diazabicyclononane, guanidine compounds such as tetramethylguanidine, triazabicyclodecene or N-methyltriazabicyclodecene.

The catalysts (E) are preferably organic dialkyltin carboxylates or reaction products thereof with alkoxysilanes, such as dioctyltin dilaurate, for example, alkyl titanates or alkyl zirconates, titanium chelates such as diisobutoxy-bisethylacetoacetato-titanates, and also reaction products of silanes or oligomers thereof, containing per molecule, as hydrolyzable groups, at least two monovalent hydrocarbyl radicals which are bonded via oxygen to silicon and which are optionally substituted by an alkoxy group, with diorganotin diacylate or diorganotin oxide.

If the materials of the invention do contain catalyst(s)(E), the amounts are preferably 0.0001 to 2 parts by weight, more preferably 0.001 to 1.5 parts by weight, based in each case on 100 parts by weight of the material of the invention.

Examples of fillers (F) are nonreinforcing fillers, these being fillers having a BET surface area of up to 50 m²/g, such as quartz, diatomaceous earth, calcium silicate, zirconium silicate, zeolites, metal oxide powders, such as aluminum, titanium, iron or zinc oxides and/or their mixed oxides, barium sulfate, calcium carbonate, gypsum, talc, kaolin, silicon nitride, silicon carbide, boron nitride, glass powders and polymeric powders, such as polyacrylonitrile powders; reinforcing fillers, these being fillers having a BET surface area of more than 50 m²/g, such as pyrogenically prepared silica, precipitated silica, precipitated calcium carbonate, carbon black, such as furnace black and acetylene black, and mixed silicon-aluminum oxides of high BET surface area; fibrous fillers, such as asbestos, and polymeric fibers. The stated fillers may have been hydrophobed, for example by treatment with organosilanes and/or organosiloxanes, or by etherification of hydroxyl groups to alkoxy groups. If fillers (F) are used, they are preferably hydrophilic fumed silica, precipitated or ground calcium carbonate, talc, and finely ground marble.

If the materials of the invention do include component (F), the amounts are preferably 5 to 200 parts by weight, more preferably 8 to 125 parts by weight, based in each case on 100 parts by weight of component (A). The materials of the invention preferably do include component (F).

The optionally employed plasticizers (G) are preferably silicone oils which are different from component (A), having viscosities of between 5 and 10,000 mPas at 25° C., or hydrocarbon mixtures having viscosities of between 1 and 20 mPas at 40° C., more preferably having viscosities of between 2 and 7 mPas at 40° C.

If plasticizers (G) are used in the process of the invention, the amounts involved are preferably 5 to 100 parts by weight, more preferably 15 to 70 parts by weight, based in each case on 100 parts by weight of component (A). In accordance with the invention it is preferred for plasticizers (G) to be used.

The adhesion promoter (H) optionally employed in the materials of the invention may comprise silanes and organopolysiloxanes having functional groups, for example those having amino, glycidyloxypropyl, ureidopropyl or methacryloyloxypropyl radicals. Examples of adhesion promoters (H) are amino-alkyl-functional silanes, such as 3-aminopropyltriethoxysilane, 3-(2-aminoethyl)-aminopropyltriethoxysilane, aminopropyltrimethoxysilane, 3-(2-aminoethyl)-aminopropyltrimethoxysilane, epoxysilanes, such as glycidyloxypropyltrimethoxysilanes, glycidyloxypropylmethyl-dimethoxysilane, glycidyloxypropyltriethoxysilane or glycidyloxypropylmethyldiethoxysilane, 2-(3-triethoxysilylpropyl)maleic anhydride, N-(3-trimethoxysilylpropyl)urea, N-(3-triethoxysilylpropyl)urea, N-(trimethoxysilylmethyl)urea, N-(methyldimethoxysilylmethyl)urea, N-(3-triethoxysilylmethyl)urea, N-(3-methyldiethoxysilylmethyl)urea, O-methylcarbamatomethyl-methyldimethoxysilane, O-methylcarbamatomethyl-trimethoxysilane, O-ethylcarbamato-methyl-methyldiethoxysilane, O-ethylcarbamatomethyl-triethoxysilane, 3-methacryloxypropyl-trimethoxysilane, methacryloyloxymethyl-trimethoxysilane, methacryloyloxymethyl-methyldimethoxysilane, methacryloyloxymethyl-triethoxysilane, methacryloyloxymethyl-methyldiethoxysilane, 3-acryloyloxypropyl-trimethoxysilane, acryloyloxymethyl-trimethoxysilane, acryloyloxymethyl-methyldimethoxysilane, acryloyloxymethyl-triethoxysilane, and acryloyloxymethyl-methyldiethoxysilane, and also their partial condensates.

If the materials of the invention do include component (H), the amounts are preferably 0.2 to 4 parts by weight, more preferably 1 to 2.5 parts by weight, based in each case on 100 parts by weight of component (A). The materials of the invention preferably do include component (J).

Examples of the stabilizers (J) optionally employed for producing the crosslinkable materials of the invention are acidic phosphoric esters, phosphonic acids, and acidic phosphonic esters.

If the materials of the invention do include component (J), the amounts are preferably 0.01 to 1 part by weight, based on 100 parts by weight of component (A). The materials of the invention preferably do include component (H).

Examples of optionally employed additives (L) are fungicides, dyes, pigments, heat stabilizers, oxidation inhibitors, organic solvents, agents for influencing electrical properties, such as conductive carbon black, flame retardants, and light stabilizers.

If the materials of the invention do include component (L), the amounts involved are preferably 0.01 to 30 parts by weight, more preferably 0.05 to 2 parts by weight, based in each case on 100 parts by weight of component (A). The materials of the invention preferably do include component (L).

The components used in preparing the crosslinkable materials of the invention may each comprise one kind of such a component or else a mixture of at least two kinds of a respective component.

The materials of the invention are preferably materials producible using
(A) organosilicon compounds comprising units of the formula (I),
(C) silanes of the formula (II),
(D) organosilicon compounds selected from the compounds (D1), (D2), (D3) or combinations thereof,
(E) optionally, catalysts,
(F) optionally, fillers
(G) optionally, plasticizers
(H) optionally, adhesion promoters
(J) optionally, stabilizers, and
(L) optionally, additives.

More preferably the crosslinkable materials of the invention are materials producible using
(A) organosilicon compounds consisting of units of the formula (I),
(C) silanes of the formula (II) where d is 1 and radical $R^7$ is alkyl radicals having 1 to 6 carbon atoms,
(D) organosilicon compounds (D1) where m is 1 and radical $R^8$ is methyl radical,
(E) optionally, catalysts,
(F) fumed silica,
(G) optionally, plasticizers,
(H) adhesion promoters, and
(J) optionally, stabilizers.

A further particularly preferred crosslinkable material is producible using
(A) organosilicon compounds consisting of units of the formula (I),
(C) silanes of the formula (II) where d is 1 and radical $R^7$ is alkyl radicals having 1 to 6 carbon atoms,
(D) a mixture of organosilicon compounds (D1) where m is 1 and radical $R^8$ is methyl radical and also (D2) where $R^{19}$ is ethyl radical and $R^{11}$ is —$CH_2$—$CH_2$—,
(E) optionally, catalysts, (F) fumed silica,
(G) optionally, plasticizers,
(H) adhesion promoters, and
(J) optionally, stabilizers.

A further particularly preferred crosslinkable material is producible using
(A) organosilicon compounds consisting of units of the formula (I),
(C) silanes of the formula (II) where d is 1 and radical $R^7$ is methyl radical,
(D) a mixture of organosilicon compounds (D3) where $R^8$ is methyl radical and $R^9$ is ethyl radical and also (D2) where $R^{10}$ is ethyl radical and $R^{11}$ is —$CH_2$—$CH_2$—,
(E) optionally catalysts,
(F) optionally, fumed silica,
(G) optionally, plasticizers,
(H) optionally, adhesion promoters, and also
(J) optionally, stabilizers.

A yet further particularly preferred crosslinkable material is producible using
(A) organosilicon compounds consisting of units of the formula (I),
(C) silanes of the formula (II) where d is 1 and radical $R^7$ is methyl radical,
(D) organosilicon compounds (D3) where $R^8$ is methyl radical and $R^9$ is ethyl radical,
(E) optionally, catalysts,
(F) optionally, fumed silica,
(G) optionally, plasticizers,
(H) optionally, adhesion promoters, and also
(J) optionally, stabilizers.

A still further particularly preferred crosslinkable material is producible using
(A) organosilicon compounds consisting of units of the formula (I),
(C) silanes of the formula (II) where d is 1 and radical $R^7$ is methyl radical,
(D) organosilicon compounds (D2) where $R^{10}$ is ethyl radical and $R^{11}$ is —$CH_2$—$CH_2$—,
(E) optionally, catalysts,
(F) fumed silica,
(G) optionally, plasticizers,
(H) adhesion promoters, and also
(J) optionally, stabilizers.

A yet still further particularly preferred crosslinkable material is producible using
(A) organosilicon compounds consisting of units of the formula (I),
(B) silanes of the formula $R^1{}_2NCR^4{}_2SiR^3(OR^2)_2$ where $R^1$ is alkyl radicals having 1 to 6 carbon atoms and $R^2$ is alkyl radicals having 1 to 4 carbon atoms,
(C) silanes of the formula (II) where d is 1 and radical $R^7$ is alkyl radicals having 1 to 6 carbon atoms,
(D) organosilicon compounds (D1) where m is 1 and radical $R^8$ is methyl radical and $R^9$ is ethyl radical,
(E) optionally, catalysts,
(F) fumed silica,
(G) optionally, plasticizers,
(H) adhesion promoters, and also
(J) optionally, stabilizers.

Another further particularly preferred crosslinkable material is producible using
(A) organosilicon compounds consisting of units of the formula (I),
(B) silanes of the formula $R^1{}_2NCR^4{}_2SiR^3(OR^2)_2$ where $R^1$ is alkyl radicals having 1 to 6 carbon atoms and $R^2$ is alkyl radicals having 1 to 4 carbon atoms,
(C) silanes of the formula (II) where d is 1 and radical $R^7$ is alkyl radicals having 1 to 6 carbon atoms,
(D) a mixture of organosilicon compounds (D1) where m is 1 and radical $R^8$ is methyl radical and also (D2) where $R^{10}$ is ethyl radical and $R^{11}$ is —$CH_2$—$CH_2$—,
(E) optionally catalysts,
(F) fumed silica,
(G) optionally, plasticizers,
(H) adhesion promoters, and also
(J) optionally, stabilizers.

Another further particularly preferred crosslinkable material is producible using
(A) organosilicon compounds consisting of units of the formula (I),
(B) silanes of the formula $R^1{}_2NCR^4{}_2SiR^3(OR^2)_2$ where $R^1$ is alkyl radicals having 1 to 6 carbon atoms and $R^2$ is alkyl radicals having 1 to 4 carbon atoms,
(C) silanes of the formula (II) where d is 1 and radical $R^7$ is alkyl radicals having 1 to 6 carbon atoms,
(D) a mixture of organosilicon compounds (D3) where $R^8$ is methyl radical and $R^9$ is ethyl radical and also (D2) where $R^{10}$ is ethyl radical and $R^{11}$ is —$CH_2$—$CH_2$—,
(E) optionally, catalysts,
(F) fumed silica,
(G) optionally, plasticizers,
(H) adhesion promoters, and also
(J) optionally, stabilizers.

Another further particularly preferred crosslinkable material is producible using
(A) organosilicon compounds consisting of units of the formula (I) preparable by reaction of organosilicon compounds having at least two OH groups (A0) with silanes (B) and silanes (C') of the formulae $R^3Si(OR^2)_3$ or $Si(OR^2)_4$, optionally in the presence of catalyst (K) and also optionally of further substances,
(C) silanes of the formula (II) where d is 1 and radical $R^7$ is alkyl radicals having 1 to 6 carbon atoms,
(D) a mixture of organosilicon compounds (D1) where m is 1 and radical $R^8$ is methyl radical and also (D2) where $R^{10}$ is ethyl radical and $R^{11}$ is —$CH_2$—$CH_2$—,
(E) optionally catalysts,
(F) fumed silica,
(G) optionally, plasticizers,
(H) adhesion promoters, and also
(J) optionally, stabilizers.

With particular preference the crosslinkable materials of the invention are materials producible using
(A) organosilicon compounds consisting of units of the formula (I),
(C) silanes of the formula (II) where d is 1 and radical $R^7$ is alkyl radicals having 1 to 6 carbon atoms,
(D) organosilicon compounds (D1) where m is 1 and radical $R^8$ is methyl radical,
(E) optionally, catalysts,
(F) chalk,
(G) optionally, plasticizers,
(H) adhesion promoters, and also
(J) optionally stabilizers.

The materials of the invention preferably contain no isocyanates. If the materials of the invention do contain isocyanates, the amounts involved are preferably not more than 25 mol %, more preferably 0 to 10 mol %, based in each case on the molar amount of the units $[R^1{}_2NCR^4{}_2]Si\equiv$, where $R^1$ and $R^4$ have the definition indicated above.

With particular preference no constituents beyond components (A) to (L) are used in producing the materials of the invention.

The organopolysiloxane compositions of the invention preferably have a viscosity of 100 to 1,000,000 mPa·s, more preferably from 1000 to 500,000 mPa·s, and most preferably from 10,000 to 250,000 mPa·s, in each case measured at 25° C. with a deformation of 100% in accordance with DIN 54458.

The materials of the invention may be produced in any desired manner, such as by simple mixing of the individual components, in which case the organopolysiloxane composition of the invention employed as component (A) may be prepared in situ. Preference is given to the prior preparation of component (A) with a lead time of at least 30 minutes, realized preferably by means of a buffer section or a buffer tank.

A further subject of the present invention is a process for producing the organopolysiloxane compositions of the invention by mixing the individual components in any desired order.

The mixing in accordance with the invention may take place at room temperature under the pressure of the surrounding atmosphere, in other words at about 900 to 1100 hPa, or under reduced pressure of about 20 hPa to 800 hPa. If desired, however, this mixing may also take place at higher temperatures, as for example at temperatures in the range from 35 to 135° C. Heating or cooling may be carried out if desired.

According to one preferred procedure of the process of the invention, in a

First Step rganosilicon compounds having at least two OH groups (A0) are mixed with silanes (B), silanes (C'), and optionally catalyst (K), and also, optionally, plasticizer (G), and left to react, and then in a Second Step the reaction material obtained in the first step is mixed with silanes (C), organosilicon compounds (D), and also, optionally, further components selected from components (E) to (L).

According to a further preferred procedure of the process of the invention, one or more devolatilizing steps take place in the second step, preferably after addition of the components (F) and optionally of further components (G), (H), (J), and (L).

The mixing of the individual components in accordance with the invention is accomplished preferably very largely with exclusion of water from the surrounding atmosphere, something which may be accomplished, for example, by blanketing with dry air or dry nitrogen.

The process of the invention can be carried out as what is called a one-pot reaction in one reaction vessel. Also possible, however, is for the individual steps of the process of the invention to be carried out separately.

Formed during the reaction in accordance with the invention are elimination products of the formulae $R^2$—OH and optionally $R^7$—OH, which may remain in the reaction material or may be removed by known methods, with $R^2$ and $R^7$ having the above-stated definition.

The process of the invention may be carried out either continuously or discontinuously.

An advantage of the process of the invention is that it is quick and easy to implement, and readily available raw materials can be used as reactants.

An advantage of the materials of the invention is that they are substantially free from isocyanates.

An advantage of the materials of the invention is that the polymers used in the crosslinkable materials have a stable viscosity, and the polymers used are highly compatible with various catalyst systems.

An advantage of the materials of the invention is that they exhibit excellent storage stability.

An advantage of the materials of the invention is that the resulting elastomer exhibits very high stability under climatic stress storage conditions.

An advantage of the materials of the invention is that they are highly workable, particularly in terms of relatively easy extrusion from containers, such as cartridges.

An advantage, furthermore, of the crosslinkable materials of the invention is that they are notable for a high crosslinking rate.

An advantage of the crosslinkable materials of the invention, in particular, is that the modulus in the crosslinking products can be adjusted easily and within wide limits.

An advantage of the crosslinkable materials of the invention, furthermore, is that polymer (A) can be prepared with a low fraction of chain-extending silanes and, accordingly, relatively low fractions of elimination products are produced.

For the crosslinking of the materials of the invention, the customary water content of the air is sufficient. Crosslinking, if desired, may also be carried out at higher or lower temperatures than room temperature, e.g., at −5 to 10° C. or at 30 to 50° C. Crosslinking is preferably carried out under the pressure of the surrounding atmosphere, in other words about 900 to 1100 hPa.

A further subject of the present invention are shaped bodies produced by crosslinking the materials of the invention.

The crosslinkable materials of the invention can be employed for all purposes for which materials which are crosslinkable at room temperature by condensation reaction are useful. They are therefore outstandingly suitable, for example, as sealing compounds for joints, including vertical joints and similar empty spaces, in, for example, buildings, land vehicles, water vehicles, and air vehicles, or as adhesives or putties, in window construction or in the production of glazed display systems, for example, and also for producing protective coatings or elastomeric moldings, and also for insulating electrical or electronic apparatus. The RTV materials of the invention are especially suitable as low-modulus sealing compounds for joints with possibility of substantial accommodation of movement.

In the examples described below, all of parts and percentages are based on weight unless otherwise indicated. Furthermore, all viscosities are based on a temperature of 25° C., unless otherwise indicated. Unless indicated otherwise, the examples below are carried out under the pressure of the surrounding atmosphere, in other words at about 1000 hPa, and at room temperature, in other words at about 20° C., or at a temperature which comes about when the reactants are combined at room temperature without additional heating or cooling.

For the purposes of the present invention, the viscosities of the siloxanes are determined as such, such as of polymers P1 to P8, for example, as follows: The dynamic viscosity measurements are based on DIN 53019-1 on a plate/cone rotational viscometer having a cone of diameter 50 mm and a cone angle of 2, at 25° C. and at a shear rate of 1 l/s to 10 l/s. Evaluation takes place via linear regression in the linear range.

The viscosities and paste properties of the crosslinkable materials of the invention are based on measurement according to DIN 54458 by means of an amplitude sweep. Measurement takes place via plate/plate with a cone of diameter 25 mm and with 0.5 mm spacing with a circular frequency of 10 Hz.

Viscosity $\eta^*(\gamma=0.1\%)$: this corresponds to the complex viscosity [mPa*s] at a deformation of 0.1% as per DIN 54458, viscosity $\eta^*(\gamma=100\%)$: this corresponds to the complex viscosity [mPa*s] at a deformation of 100% as per DIN 54458.

The weight-average molar mass $M_w$ and number-average molar mass $M_n$ are determined for the purposes of the present invention by means of Size Exclusion Chromatography (SEC) against polystyrene standards, in THF, at 60° C., with flow rate of 1.2 ml/min and with detection by RI (refractive-index detectors) on a Styragel HR3-HR4-HR5-HR5 column set from Waters Corp. USA, with an injection volume of 100 µl.

In the preparation of the polymers P1 to P8, the chain extension (CE) fraction is computed from the molar ratio of component (B) to the SiOH content of component A0.

The skin-forming time is defined as the time after which there is no longer any adhering residue of a delivered string of silicone to a pencil of hardness HB with which it is contacted.

The early strength is determined by applying a strip of silicone 10 mm wide and 6 mm in height to a plate of aluminum 0.25 mm thick, using a doctor blade, then bending one specimen by 90° at 30-minute intervals. The early strength reported is the time required for the silicone strip to no longer exhibit any tear.

The Shore A hardness is determined according to DIN (Deutsche Industrie Norm—German Industry Standard) 53505-87.

The elongation at break, tensile strength, and strain at 100% elongation are determined according to DIN 53504-85S2.

The 100% strain value corresponds to the secant modulus at an elongation of 100%.

Hardness, elongation at break, 100% strain value, and tensile strength after climatic stress storage at 7d/70° C./95% rh are determined according to DIN 53505-87 and DIN 53504-85S2, respectively, with the specimens initially vulcanizing for 14 days at 23° C./50% relative atmospheric humidity and then being stored in a climate cabinet for 7 days at 70° C. and 95% relative atmospheric humidity. After a rest time of 1 hour in the 23° C./50% relative atmospheric humidity standard conditions, the specimens are measured as prescribed in the standard.

The examples use the following abbreviations or terms:
Me is the methyl radical,
Et is the ethyl radical, Yield point: this corresponds to the shear stress [Pa] at the point of the value tan d=1, at which the ratio of loss modulus to storage modulus is equal to 1.

Preparation of Polymer P1

420 parts by weight of an α,ω-dihydroxy-dimethylpolysiloxane having a viscosity of 80,000 mPa·s are mixed with a mixture of 0.6 part by weight of a silane of the formula $(CH_3CH_2)_2N—CH_2—Si(CH_3)(OCH_2CH_3)_2$, 30 parts by weight of methyltrimethoxysilane and 0.15 part by weight of zinc acetylacetonate in a planetary mixer. The viscosity of the polymer mixture was determined as a function of time and reproduced in Table 1.

Preparation of Polymer P2

420 parts by weight of an α,ω-dihydroxy-dimethylpolysiloxane having a viscosity of 80,000 mPa·s (OH content 470 ppm by weight) are homogenized with a mixture of 0.45 part by weight of a silane of the formula $(C_2H_5)_2N—CH_2—Si(CH_3)(OCH_2CH_3)_2$, 14 parts by weight of vinyltrimethoxysilane and 0.07 part by weight of zinc acetylacetonate in a planetary mixer. The viscosity of the polymer mixture was determined as a function of time and reproduced in Table 1.

Preparation of Polymer P3

420 parts by weight of an α,ω-dihydroxy-dimethylpolysiloxane having a viscosity of 80,000 mPa·s (OH content 470 ppm by weight) are mixed with a mixture of 0.28 part by weight of a silane of the formula $(CH_3CH_2)_2N—CH_2—Si(CH_3)(OCH_2CH_3)_2$ and 30 parts by weight of methyltrimethoxysilane and 0.15 parts by weight of zinc acetylacetonate, added for catalysis, in a planetary mixer. The viscosity of the polymer mixture was determined as a function of time and reproduced in Table 1.

Preparation of Polymer P4

420 parts by weight of an α,ω-dihydroxy-dimethylpolysiloxane having a viscosity of 80,000 mPa·s (OH content 470 ppm by weight) are homogenized with a mixture of 0.19 parts by weight of a silane of the formula $(C_2H_5)_2N—CH_2—Si(CH_3)(OCH_2CH_3)_2$, 14 parts by weight of vinyltrimethoxysilane, 4 parts by weight of methyltrimethoxysilane and 0.07 part by weight of zinc bisacetylacetonate in a planetary mixer. The viscosity of the polymer mixture was determined as a function of time and reproduced in Table 1.

Preparation of Polymer P5

420 parts by weight of an α,ω-dihydroxy-dimethylpolysiloxane having a viscosity of 80,000 mPa·s (OH content 470 ppm by weight) are mixed with a mixture of 0.1 part by weight of a silane of the formula $(CH_3CH_2)_2N—CH_2—Si(CH_3)(OCH_2CH_3)_2$ and 30 parts by weight of methyltrimethoxysilane and 0.15 part by weight of zinc acetylacetonate, for catalysis, in a planetary mixer. The viscosity of the polymer mixture was determined as a function of time and reproduced in Table 1.

Preparation of Polymer P6

420 parts by weight of an α,ω-dihydroxy-dimethylpolysiloxane having a viscosity of 80,000 mPa·s are mixed with a mixture of 0.35 part by weight of a silane of the formula $(CH_3CH_2)_2N—CH_2—Si(CH_3)(OCH_2CH_3)_2$, 30 parts by weight of methyltrimethoxysilane and 0.15 part by weight of zinc acetylacetonate in a planetary mixer. The viscosity of the polymer mixture was determined as a function of time and reproduced in Table 1.

Preparation of Polymer P7

420 parts by weight of an α,ω-dihydroxy-dimethylpolysiloxane having a viscosity of 80,000 mPa·s are mixed with a mixture of 0.35 part by weight of a silane of the formula $(CH_3CH_2)_2N—CH_2—Si(CH_3)(OCH_2CH_3)_2$, 0.3 part by weight of cyclohexyl isocyanate, 30 parts by weight of methyltrimethoxysilane and 0.15 part by weight of zinc acetylacetonate in a planetary mixer. The viscosity of the polymer mixture was determined as a function of time and reproduced in Table 1.

Preparation of Polymer P8

420 parts by weight of an α,ω-dihydroxy-dimethylpolysiloxane having a viscosity of 80,000 mPa·s are homogenized with a mixture of 14 parts by weight of vinyltrimethoxysilane, 4 parts by weight of methyltrimethoxysilane and 0.07 part by weight of zinc acetylacetonate in a planetary mixer. The viscosity of the polymer mixture was determined as a function of time and reproduced in Table 1.

TABLE 1

Viscosity profile

|  | Polymer | | | |
|---|---|---|---|---|
|  | P1 | P2 | P3 | P4 |
| Fraction of chain extension | 23% | 17% | 11% | 7% |
| OH content [ppm] | 470 | 470 | 470 | 470 |
| Dyn. viscosity after preparation [mPa * s] | 77,300 | 76,200 | 76,600 | 69,200 |
| Dyn. viscosity after 21 days [mPa * s] | 73,800 | 70,200 | 73,700 | 67,200 |
| Dyn. viscosity after 7 days at 50° C. [mPa * s] | 67,200 | 69,300 | 70,900 | 64,100 |
| Δη (after 7 d/50° C.) | −13% | −9% | −7% | −7% |

|  | Polymer | | | |
|---|---|---|---|---|
|  | P5 | P6 | P7 | P8 |
| Fraction of chain extension | 4% | 13% | 13% | 0% |
| OH content [ppm] | 470 | 470 | 470 | 470 |
| Dyn. viscosity after preparation [mPa * s] | 71,200 | 73,000 | 72,400 | 59,900 |
| Dyn. viscosity after 21 days [mPa * s] | 70,200 | 70,400 | 68,100 | 69,600 |
| Dyn. viscosity after 7 days at 50° C. [mPa * s] | 69,700 | 67,300 | 66,500 | 73,600 |
| Δη (after 7 d/50° C.) | −2% | −8% | −7% | +23% |

The examples exhibit high polymer stability, meaning low deviations in viscosity after 7 days at 50° C.

A noninventive, comparative mixture P8 without chain extender, in contrast, undergoes a significant increase in viscosity. The isocyanate-containing mixture P7 shows no significant advantages in stability of viscosity relative to P6.

INVENTIVE EXAMPLE 1

After the polymers prepared above have been aged for a time of 24 hours, 230 g of polymer P1 are mixed with 84 g of a trimethylsilyl-terminal dimethylpolysiloxane having a viscosity of 1000 mPa·s, and 3 g of N-aminoethyl-aminopropyltrimethoxysilane and 4 g of vinyltrimethoxysilane are added. To this were added 3 g of component (D1), consisting of 16.0 mol % of units of the formula $MeSi(OEt)_2O_{1/2}$, 46.4 mol % of units of the formula $MeSi(OEt)O_{2/2}$ and 36.5 mol % of units of the formula $MeSiO_{3/2}$ and also 0.2 mol % of the formula $(Me)_2Si(OEt)O_{1/2}$ and 0.9 mol % of the formula $Me_2SiO_{2/2}$. Then 32 g of a fumed silica having a BET surface area of 150 m²/g are mixed in homogeneously, and 1 g of a tin catalyst, prepared by reaction of di-n-butyltin diacetate and tetraethoxysilane, and 0.5 g of octylphosphonic acid are added. The mixture is devolatilized under a pressure of 100 mbar for 5 minutes.

The rheology of the resulting material is characterized according to DIN 54458. Furthermore, the elastomer properties are determined on 2 mm vulcanizate sheets according to DIN 53504. The sheets are produced by vulcanization of a 2 mm layer, applied to PE film, at 23° C./50% relative atmospheric humidity.

The storage stability was determined by accelerated aging of the paste in cartridges at 70° C.

The properties are set out in Table 2.

INVENTIVE EXAMPLES 2 TO 6

The procedure described in inventive example 1 is repeated in each case, with the modification that polymers P2 to P6 were used instead of polymer P1. The results are found in Table 2.

INVENTIVE EXAMPLE 7

The procedure described in inventive example 1 is repeated, with the modification that rather than 3 g only 2 g of component (D1) were used, consisting of 16.0 mol % of units of the formula $MeSi(OEt)_2O_{1/2}$, 46.4 mol % of units of the formula $MeSi(OEt)O_{2/2}$ and 36.5 mol % of units of the formula $MeSiO_{3/2}$ and also 0.2 mol % of the formula $(Me)_2Si(OEt)O_{1/2}$ and 0.9 mol % of the formula $Me_2SiO_{2/2}$, and additionally 1 g of component (D2) $(MeO)_3Si-CH_2-CH_2-Si(OMe)_3$ was used.

INVENTIVE EXAMPLE 8

The procedure described in inventive example 1 is repeated, with the modification that a combination of 1 part of (D2) where $R^{10}$=Me and $R^{11}$=—$CH_2$—$CH_2$— and also 2 parts of (D3) with 54 mol % of $MeSiO_{1/2}$ units, 42 mol % of $SiO_{4/2}$ units and 4 mol % of $Si(OEt)O_{3/2}$ units is used.

COMPARATIVE EXAMPLE C1

The procedure described in inventive example 1 is repeated, with the modification that polymer P8 is used.

COMPARATIVE EXAMPLE C2

The procedure described in inventive example 1 is repeated, with the modification that no component (D1) is used.

COMPARATIVE EXAMPLE C3

The procedure described in inventive example 6 is repeated, with the modification that no component (D1) is used.

COMPARATIVE EXAMPLE C4

The procedure described in comparative example C1 is repeated, with the modification that a polymer component P9 was prepared in the same way as for P8, with the difference that a mixture of 280 parts by weight of an α,ω-dihydroxy-dimethylpolysiloxane having a viscosity of 80,000 mPa·s and 140 parts by weight of an α,ω-dihydroxy-dimethylpolysiloxane having a viscosity of 350,000 mPa·s is used.

TABLE 2

| Example | 1 | 2 | 3 | 4 | 5 | 6 |
|---|---|---|---|---|---|---|
| CE fraction | 23% | 17% | 11% | 7% | 4% | 13% |
| Viscosity η* (γ = 0.1%) | 608,100 | 624,000 | 563,300 | 546,000 | 582,400 | 589,200 |
| Viscosity η* (γ = 100%) | 72,000 | 76,100 | 64,200 | 65,800 | 67,700 | 71,300 |

TABLE 2-continued

| | | | | | | |
|---|---|---|---|---|---|---|
| Yield point | 1410 | 1490 | 1510 | 1610 | 1750 | 1420 |
| Skin-forming time | 14 | 15 | 18 | 17 | 17 | 14 |
| Early strength | 30 | 30 | 30 | 30 | 30 | 30 |
| Shore A hardness | 12 | 14 | 16 | 17 | 21 | 10 |
| Elongation at break % | 660 | 580 | 490 | 450 | 360 | 790 |
| Tensile strength | 1.0 | 1.1 | 1.1 | 1.2 | 1.3 | 0.9 |
| 100% strain value | 0.18 | 0.23 | 0.26 | 0.28 | 0.34 | 0.13 |
| Paste storage 28 d at 50° C. | | | | | | |
| Skin-forming time | 17 | 16 | 20 | 15 | 19 | 15 |
| Climate storage vulcanizate 7 d at 70° C./95% rh | | | | | | |
| Hardness | 8 | 12 | 14 | 15 | 15 | 7 |
| Elongation at break | 730 | 630 | 670 | 580 | 500 | 860 |
| Tensile strength | 0.9 | 1.0 | 1.0 | 1.1 | 1.1 | 0.9 |
| 100% strain value | 0.14 | 0.19 | 0.21 | 0.22 | 0.24 | 0.10 |

| Example | 7 | 8 | C1 | C2 | C3 | C4 |
|---|---|---|---|---|---|---|
| CE fraction | 23% | 23% | 0% | 23% | 32% | 0% |
| Viscosity $\eta^*$ ($\gamma = 0.1\%$) | 586,500 | 645,700 | 729,000 | 603,100 | 583,400 | 860,200 |
| Viscosity $\eta^*$ ($\gamma = 100\%$) | 69,200 | 81,600 | 86,000 | 79,300 | 68,500 | 124,000 |
| Yield point | 1380 | 1640 | 1700 | 1680 | 1410 | 1310 |
| Skin-forming time | 15 | 15 | 17 | 15 | 15 | 13 |
| Early strength | 30 | 30 | 60 | 30 | 30 | 60 |
| Shore A hardness | 15 | 14 | 21 | 11 | 9 | 16 |
| Elongation at break % | 580 | 610 | 310 | 650 | 870 | 480 |
| Tensile strength | 1.3 | 1.2 | 1.2 | 1.3 | 1.1 | 1.2 |
| 100% strain value | 0.22 | 0.19 | 0.39 | 0.21 | 0.12 | 0.26 |
| Paste storage 28 d at 50° C. | | | | | | |
| Skin-forming time | 13 | 15 | 20 | 20 | 19 | 17 |
| Climate storage vulcanizate 7 d at 70° C./95% rh | | | | | | |
| Hardness | 12 | 12 | 16 | 3 | 2 | 13 |
| Elongation at break | 660 | 690 | 340 | 60 | 90 | 540 |
| Tensile strength | 1.1 | 1.0 | 1.1 | 0.2 | n.m | 1.0 |
| 100% strain value | 0.17 | 0.15 | 0.33 | n.m | n.m | 0.18 |

The modulus of the materials of the invention can be adjusted across a wide range.

The stability of the inventive materials after climatic storage of the vulcanizates is evident from comparing inventive examples 7 and 8 with comparative example C2, and C3 with inventive example 6: whereas the initial properties are comparable, the elastomer properties such as hardness, tensile strength, elongation at break, and 100% strain value suffer a massive collapse in the case of the noninventive materials.

The improved working characteristics are evident from the lower viscosity $\eta^*$ at $\gamma=0.1\%$ and $\gamma=100\%$ in conjunction with high yield point.

The high vulcanization rate is evident from the short skin-forming times and the short early strengths.

The skin-forming times are stable (see table); the early strengths after aging of the pastes for 28 d at 50° C. are unchanged.

The invention claimed is:

1. A crosslinkable organopolysiloxane composition produced from (A) organosilicon compounds comprising units of the formula $$[R^1{}_2NCR^4{}_2]_bSiR^3{}_c(OR^2)_aO_{(4-a-b-c)/2} \qquad (I),$$

where $R^1$ each is identical or different and is a monovalent, optionally substituted hydrocarbyl radical, $R^2$ each is identical or different and is a monovalent, optionally substituted hydrocarbyl radical, $R^3$ each is identical or different and is a monovalent hydrocarbyl radical, $R^4$ each is identical or different and is hydrogen or a monovalent, optionally substituted hydrocarbyl radical, a is 0, 1, 2 or 3, b is 0, 1 or 2, and c is 0, 1, 2 or 3, with the proviso that organosilicon compound (A) has at least one unit of the formula (I) where a=b=c=1, the sum of a+b+c=2 in at least 50% of the units of the formula (I), and the organosilicon compound contains at least 2 groups —$OR^2$;

optionally, (B) one or more silanes of the formula $$R^1{}_2NCR^4{}_2SiR^3(OR^2)_2 \qquad (XI),$$

where $R^1$, $R^2$, $R^3$, and $R^4$ are each identical or different and have one of the definitions indicated above, (C) one or more silanes of the formula $$R^6{}_dSi(OR^7)_{4-d} \qquad (II)$$

and/or partial hydrolysates thereof having up to 10 silicon atoms, where $R^6$ has a definition indicated for $R^3$, $R^7$ each is identical or different and is a monovalent, optionally substituted hydrocarbyl radical or a radical —$N{=}CR^5{}_2$, $R^5$ each is identical or different and has a definition indicated for $R^2$, and d is 0 or 1;

and (D) one or more organosilicon compounds selected from the group consisting of (D1) compounds comprising units of the formulae $$R^8{}_mSi(OR^9)_{3-m}O_{1/2} \qquad (III),$$

$$R^8{}_mSi(OR^9)_{2-m}O_{2/2} \qquad (IV), and$$

$$R^8{}_mSi(OR^9)_{1-m}O_{3/2} \qquad (V),$$

where $R^8$ each is identical or different and is a monovalent hydrocarbyl radical, $R^9$ each is identical or different and is a monovalent hydrocarbyl radical, and m in each case is 0 or 1, with the proviso that compound (D1) has at least 3 groups —$OR^9$ per molecule and has a weight-average molecular weight Mw of 1000 to 3000 g/mol, (D2) compounds of the formula $$(R^{10}O)_3Si{-}R^{11}{-}Si(OR^{10})_3 \qquad (VII),$$

where $R^{10}$ each is identical or different and is a monovalent, optionally substituted hydrocarbyl radical optionally interrupted by one or more heteroatoms, $R^{11}$ each is identical or different and is a divalent, optionally substituted hydrocarbyl radical optionally interrupted by one or more heteroatoms,
and
(D3) compounds comprising units of the formulae

$R^8{}_3SiO_{1/2}$ (XII),

$SiO_{4/2}$ (VI), and

$R^8{}_mSi(OR^9)_{1-m}O_{3/2}$ (V)

and also, optionally, further comprising units of the formulae (III) and (IV),
where
$R^8$, $R^9$ and m have a definition indicated for them above, with the proviso that m is 0 and compound (D3) has at least 3 groups —$OR^9$ per molecule and has a weight-average molar weight Mw of 1000 to 4000 g/mol.

2. The organopolysiloxane composition of claim 1, wherein organosilicon compounds (A) are prepared by reaction of organosilicon compounds having at least two OH groups (A0) with silanes (B) and silanes (C') of the formula $R^3Si(OR^2)_3$ and/or $Si(OR^2)_4$, optionally in the presence of catalyst (K) and, optionally, in the presence of further substances, and $R^2$ and $R^3$ have one of the definitions indicated for them above.

3. The organopolysiloxane composition of claim 2, wherein one or more silanes (B) are present in an amount such that the molar ratio of component (B) to Si—OH in component (A0) is less than 1.

4. The organopolysiloxane composition of claim 3, wherein radical $R^7$ comprises alkyl radicals having 1 to 6 carbon atoms.

5. The organopolysiloxane composition of claim 3, wherein component (D) comprises exclusively compounds (D1), or exclusively compounds (D2), or a mixture of compounds (D1) and (D2).

6. The organopolysiloxane composition of claim 2, wherein radical $R^7$ comprises alkyl radicals having 1 to 6 carbon atoms.

7. The organopolysiloxane composition of claim 2, wherein component (D) comprises exclusively compounds (D1), or exclusively compounds (D2), or a mixture of compounds (D1) and (D2).

8. The organopolysiloxane composition of claim 1, wherein radical $R^7$ comprises alkyl radicals having 1 to 6 carbon atoms.

9. The organopolysiloxane composition of claim 1, wherein component (D) comprises exclusively compounds (D1), or exclusively compounds (D2), or a mixture of compounds (D1) and (D2).

10. The organopolysiloxane composition of claim 1, wherein the composition comprises isocyanates in amounts of not more than 25 mol %, based on the molar amount of the units $[R^1{}_2NCR^4{}_2]Si\equiv$.

11. A process for producing an organopolysiloxane composition of claim 1, comprising mixing the individual components in any desired order.

12. The process of claim 11, wherein, in a first step organosilicon compounds having at least two OH groups (A0) are mixed with silanes (B), silanes (C), and optionally catalyst (K), and also, optionally, plasticizer (G), and left to react to obtain organosilicon compounds (A), and then in a second step
the reaction material obtained in the first step is mixed with silanes (C), organosilicon compounds (D), and also, optionally, further components selected from components
(E) catalysts,
(F) fillers,
(G) plasticizers,
(H) adhesion promoters
(J) stabilizers, and
(L) additives.

13. A shaped body produced by crosslinking an organopolysiloxane composition prepared by the process of claim 11.

14. A shaped body produced by crosslinking an organopolysiloxane composition of claim 1.

15. The organopolysiloxane composition of claim 1, wherein component (D) comprises a mixture of D2 and D3.

* * * * *